United States Patent [19]

Hori et al.

[11] Patent Number: 4,605,559

[45] Date of Patent: Aug. 12, 1986

[54] COMPOUND, FR-900447, PRODUCTION AND USE THEREOF

[75] Inventors: Yasuhiro Hori, Toyonaka; Motohiro Hino, Ikeda; Hiroshi Terano, Toyonaka; Masashi Hashimoto, Takarazuka; Masanobu Kohsaka, Sakai, all of Japan

[73] Assignee: Fujisawa Pharmaceutical Co., Ltd., Osaka, Japan

[21] Appl. No.: 646,090

[22] Filed: Aug. 31, 1984

[30] Foreign Application Priority Data

Sep. 7, 1983 [GB] United Kingdom ............... 8324006

[51] Int. Cl.$^4$ .................. A61K 35/74; C12P 1/06

[52] U.S. Cl. .................................... 424/120; 435/169

[58] Field of Search ...................... 424/120; 435/169

Primary Examiner—Jerome D. Goldberg
Attorney, Agent, or Firm—Oblon, Fisher, Spivak, McClelland & Maier

[57] ABSTRACT

The invention relates to a new compound, FR-900447, and pharmaceutically acceptable salts thereof having antimicrobial and antitumor activity, to a pharmaceutically composition thereof, and to a process for production thereof by culturing Streptomyces rubropurpureus FERM BP-584 in nutrient medium under aerobic condition.

3 Claims, No Drawings

COMPOUND, FR-900447, PRODUCTION AND USE THEREOF

This invention relates to a new compound, FR-900447. More particularly, it relates to a new compound, FR-900447 and pharmaceutically acceptable salt thereof which have antimicrobial activity and antitumor activity, to a process for the preparation thereof and to pharmaceutical composition thereof.

Accordingly, one object of this invention is to provide a new compound, FR-900447 and pharmaceutically acceptable salt thereof which have antimicrobial activity and antitumor activity, and are useful for the treatment of infectious diseases and tumors in human beings and animals.

Another object of this invention is to provide a process for preparing FR-900447 by culturing a FR-900447 producing strain belonging to the genus Streptomyces in a nutrient medium.

A further object of this invention is to provide a pharmaceutical composition comprising FR-900447 or pharmaceutically acceptable salt thereof as an active ingredient.

According to this invention the FR-900447 can be prepared by culturing a FR-900447 producing strain belonging to the genus Streptomyces such as *Streptomyces rubropurpureus* and the like in a nutrient medium.

Particulars of microorganism used for producing FR-900447 and production thereof will be explained in the followings.

MICROORGANISM

The microorganism which can be used for the production of FR-900447 is a FR-900447 producing strain belonging to the genus Streptomyces, among which *Streptomyces rubropurpureus* No. 6362 has been newly isolated from a soil sample collected in Kawachinagano city, Japan.

A lyophilized sample of the newly isolated microorganism has been deposited with an international depositary authority on the Budapest Treaty, Fermentation Research Institute, Agency of Industrial Science and Technology, Yatabe-cho higashi No. 1-1-3, Tsukuba-gun, Ibaraki-ken, Japan, under the number FERM BP-584 on Aug. 26, 1983.

It is to be understood that the production of the new compound, FR-900447 is not limited to the use of the particular organism described herein, which is given for illustrative purpose only. This invention also includes the use of any mutants which are capable of producing the FR-900447 including natural mutants as well as artificial mutants which can be produced from the described organism by conventional means, such as X-rays, ultra-violet radiation, treatment with N-methyl-N'-nitro-N-nitrosoguanidine, 2-aminopurine and the like.

*Streptomyces rubropurpureus* No. 6362 has the following morphological, cultural, biological and physiological characteristics.

The methods described by Shirling and Gottlieb [Vide. International Journal of Systematic Bacteriology 16, 313–340 (1966)] employed principally for this taxonomic study.

1. Morphological Characteristics

Morphological observations were made with light and electron microscopes on cultures grown at 30° C. for 14 days on yeast-malt extract agar, oatmeal agar or inorganic salts-starch agar. The mature spores occurred in chain of about 10 spores forming *Spirals*. The spores were cylindrical or oval and $0.5$–$0.7 \times 0.7$–$0.9$ μm in size by electron microscopic observation. Spore surfaces were smooth.

2. Cultural Characteristics

Cultural characteristics were observed on ten kinds of media described by Shirling and Gottlieb (Vide. the same literature as mentioned above) and Waksman [Vide. The Actinomycetes Vol. 2 (1961)].

The incubation was made at 30° C. for 14 days. The color names used in this study were based on Color Standard (Nihon Shikisai Co., Ltd.). Colonies belonged to the gray color series when grown on oatmeal agar, yeast-malt extract agar and inorganic salts-starch agar. No soluble pigment was produced in yeast-malt extract agar and others. Results were shown in Table 1.

TABLE 1

Cultural characteristics of strain No. 6362, *Streptomyces libani* subsp. *libani* IFO 13452 and *Streptomyces pulcher* IFO 13462

| | | No. 6362 | IFO 13452 | IFO 13462 |
|---|---|---|---|---|
| Oatmeal agar | G | moderate | moderate | poor |
| | A | pale reddish brown | pale reddish brown | olive gray |
| | R | colorless | pale yellow | colorless |
| | S | none | none | none |
| Yeast-malt extract agar | G | abundant | abundant | abundant |
| | A | pale reddish brown | grayish white to pale brown | gray |
| | R | pale yellowish brown | dark yellow orange | yellowish gray |
| | S | none | none | none |
| Inorganic salts-starch agar | G | abundant | abundant | moderate |
| | A | grayish yellow brown | pale reddish brown | dark olive gray |
| | R | grayish red purple | pale yellow | colorless |
| | S | none | none | none |
| Glucose-asparagine agar | G | abundant | moderate | moderate |
| | A | pale reddish brown | grayish white | grayish white |
| | R | pale yellow orange | pale yellow orange | pale yellow |
| | S | none | none | none |
| Glycerin-asparagine agar | G | abundant | abundant | moderate |
| | A | pale yellow orange to light gray | grayish white to grayish yellow | olive gray |
| | R | reddish orange | pale yellow orange | pale yellow |
| | S | none | pale yellow orange | none |
| Sucrose-nitrate agar | G | abundant | abundant | poor |
| | A | pale pink to grayish white | white | grayish white |
| | R | dark brown | yellowish white | pale white |

TABLE 1-continued

Cultural characteristics of strain No. 6362, *Streptomyces libani* subsp. *libani*
IFO 13452 and *Streptomyces pulcher* IFO 13462

|  |  | No. 6362 | IFO 13452 | IFO 13462 |
|---|---|---|---|---|
| Nutrient agar | S | faint brown | none | none |
|  | G | moderate | moderate | moderate |
|  | A | pale reddish brown | grayish white | grayish white |
|  | R | pale yellow orange | pale yellow | pale pink |
| Potato-dextrose agar | S | pale yellow orange | none | none |
|  | G | moderate | moderate | moderate |
|  | A | light gray, poor | grayish white | none |
|  | R | deep red purple | pale yellowish brown | pale yellow |
| Tyrosine agar | S | none | none | none |
|  | G | abundant | moderate | abundant |
|  | A | pale cinnamon pink | grayish white | grayish white |
|  | R | dark red | pale yellow brown | pale yellow orange |
| Peptone-yeast extract-iron agar | S | none | none | none |
|  | G | moderate | poor | moderate |
|  | A | none | none | grayish white |
|  | R | pale yellow | pale yellow | pale yellow orange |
|  | S | none | none | none |

Abbreviation:
G = growth,
A = aerial mass color,
R = reverse side color,
S = soluble pigment The whole cell analysis was performed by the methods of Bekcer et al [Vide. Applied Microbiology 22, 421–423 (1964)] and Yamaguchi [Vide. Journal of Bacteriology 89, 444–453 (1964)]. Analysis of whole cell hydrolysates of strain No. 6362 showed that it contained LL-diaminopimeric acid. Accordingly, the cell wall of this strain is believed to be of type I.

3. Biological and Physiological Properties

Physiological properties of strain No. 6362 were shown in Table 2. Temperature range and optimum temperature for growth were determined on yeast-malt extract agar using a temperature gradient incubator (Toyo Kagaku Sangyo Co., Ltd.). Temperature range for growth was from 14° C. to 42° C. with optimum at 32° C. Starch hydrolysis, melanin production, H₂S production, milk peptonization and milk coagulation were negative.

TABLE 2

Physiological properties of strain No. 6362,
*Stereptomyces libani* subsp. *libani* IFO 13452 and
*Streptomyces pulcher* IFO 13462

|  | No. 6362 | IFO 13452 | IFO 13462 |
|---|---|---|---|
| Temperature range for growth | 14° C.–42° C. | 13° C.–36° C. | 14° C.–43° C. |
| Optimum temperature | 32° C. | 26° C.–30° C. | 32° C.–34° C. |
| Nitrate reduction | positive | negative | negative |
| Starch hydrolysis | negative | positive | positive |
| Milk coagulation | negative | negative | negative |
| Milk peptonization | negative | negative | negative |
| Melanin production | negative | negative | negative |
| Gelatin liquefaction | negative | negative | negative |
| H$_2$S production | negative | negative | negative |
| Urease reaction | positive | negative | negative |
| NaCl tolerance (%) | 10%< | 10%< | 7%<>10% |

Utilization of carbon sources was examined according to the methods of Pridham and Gottlieb [Vide. Journal of Bacteriology 56, 107–114 (1948)]. The results were determined after 14 days incubation at 30° C. Almost all carbon sources were utilized except chitin and cellulose. Summarized carbon utilization of this strain is shown in Table 3.

TABLE 3

Carbon sources utilization of strain No. 6362,
*Streptomyces libani* subsp. *libani* IFO 13452
and *Streptomyces pulcher* IFO 13462.

|  | No. 6362 | IFO 13452 | IFO 13462 |
|---|---|---|---|
| D-Glucose | + | + | + |
| Sucrose | + | + | − |
| Glycerin | + | + | + |
| D-Xylose | + | ± | + |
| D-Fructose | + | + | + |
| Lactose | + | + | + |
| Maltose | + | + | + |
| Rhamnose | + | − | + |
| Raffinose | + | + | − |
| D-Galactose | + | + | + |
| L-Arabinose | + | + | + |
| D-Mannose | + | + | + |
| D-Trehalose | + | + | + |
| Inositol | + | + | − |
| Mannitol | + | + | + |
| Inulin | + | ± | − |
| Cellulose | − | − | − |
| Salicin | + | + | ± |
| Chitin | − | − | − |
| Sodium citrate | + | − | + |
| Sodium succinate | + | + | + |
| Sodium acetate | + | − | ± |

Symbols:
+ = utilization,
± = doubtful utilization,
− = no utilization

Microscopic studies and cell wall composition analysis of strain No. 6362 indicate that this strain belongs to the genus Streptomyces. Accordingly, a comparison of this strain was made with the published description [Vide. International Journal of Systematic Bacteriology 18, 16–189, 279–392 (1968) and 19, 391–512 (1969), Bergey's Manual of Determinative Bacteriology 8th edition (1974)] of various Streptomyces species. Strain No. 6362 is considered to resemble *Streptomyces libani* subsp. *libani* Baldacci Grein and *Streptomyces pulcher* Routien. These two species were differentiated from strain No. 6362 in the following points.

*Streptomyces libani* subsp. *libani* IFO 13452

Aerial mass color of *S. libani* subsp. *libani* is different on glucose-asparagine agar, nutrient agar and tyrosine agar. Reverse side color of *S. libani* subsp. *libani* is different on inorganic salts-starch agar, sucrose-nitrate agar and tyrosine agar. Starch hydrolysis is positive. Nitrate reduction and urease reaction are negative. *S. libani* subsp. *libani* can not assimilate rhamnose, sodium citrate and sodium acetate.

*Streptomyces pulcher* IFO 13462

Aerial mass color of *S. pulcher* is different on 8 media. Reverse side color of *S. pulcher* is different on inorganic salts-starch agar, sucrose-nitrate agar and tyrosine agar. Starch hydrolysis is positive. Nitrate reduction, urease reaction and 10% NaCl tolerance are negative. *S. pulcher* can not assimilate sucrose, raffinose, inositol and inulin.

As the results of the above comparison, it was concluded that strain No. 6362 can be considered a new species and the strain has been designated as *Streptomyces rubropurpureus* sp. nov. referring to the color of vegetative mycelium on inorganic salts-starch agar and sucrose-nitrate agar.

PRODUCTION OF FR-900447

The new compound, FR-900447 can be produced by culturing a FR-900447 producing strain belonging to the genus Streptomyces, such as *Streptomyces rubropurpureus* in a nutrient medium.

In general, FR-900447 can be produced by culturing a FR-900447 producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR-900447. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR-900447. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR-900447.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced FR-900447 can be recovered from the culture medium by conventional means which are commonly used for the recovery of other fermentation products such as antibiotics.

In general, most of the FR-900447 produced are found in the culture filtrate, and accordingly FR-900447 can be isolated from the filtrate, which is obtained by filtrating or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The FR-900447 obtained in its free form may also be converted to its acid addition salts or its base salts by treating FR-900447 with an inorganic or organic acid such as hydrochloric acid, sulfuric acid, acetic acid, p-toluene sulfonic acid and the like, or with an inorganic or organic base such as sodium hydroxide, potassium hydroxide, ethanolamine and the like. The FR-900447 as obtained according to the aforementioned process has the following physical and chemical properties;

(1) Elemental Analysis (%): C 59.05; H 6.72; N 5.57

(2) Molecular weight: 928 [SIMS: m/z 929 (M$^+$+1)]

(3) Melting point: 85° C. (dec.)

(4) Specific rotation: $[\alpha_D^{23°}] = +291.4°$ (C=0.675, H$_2$O)

(5) Ultraviolet absorption spectrum: $\lambda_{max}^{H2O}$=276 nm (E$_{1cm}^{1\%}$=390), 340nm (sh) (E$_{1cm}^{1\%}$=80); $\lambda_{max}^{H2O+HCl}$=272 nm (E$_{1cm}^{1\%}$=400), 330 nm (sh) (E$_{1cm}^{1\%}$=81); $\lambda_{max}^{H2O+NaOH}$=243 nm (E$_{1cm}^{1\%}$=275), 278 nm(E$_{1cm}^{1\%}$=350), 410 nm (E$_{1cm}^{1\%}$=31);

(6) Infrared absorption spectrum: $\nu_{max}^{KBr}$=3400, 2950, 1650, 1560, 1465, 1435, 1395 (sh), 1375, 1280, 1150, 1075, 1040 (sh), 960, 895, 855, 840 cm$^{-1}$.

(7) Nuclear magnetic resonance absorption spectrum: δppm (pyridine-d$_5$): 10.62 (1H, t, J=6Hz), 8.38 (1H, s), 8.14 (1H, s), 6.90 (1H, s), 6.895 (1H, d, J=5Hz), 6.43 (1H, s), 5.79 (1H, m), 5.80 (1H, d, J=10Hz), 5.37 (1H, d, J=5Hz), 4.48 (1H, q, J=6Hz), 4.15 (1H, m), 3.9 (2H, m), 3.85 (1H, s), 3.63 (1H, t, J=10Hz), 3.47 (1H, m), 3.34 (1H, m), 3.12 (1H, m), 3.08 (2H, m), 3.07 (3H, s), 2.9 (1H, m), 2.82 (2H, m), 2.76 (6H, s), 2.74 (1H, m), 2.50 (6H, s), 2.19 (3H, s), 1.71 (3H, d, J=6Hz), 1.63 (2H, m), 1.62 (3H, d, J=6Hz), 1.47 (3H, d, J=5.4Hz), 1.20 (3H, s).

(8) Solubility:

Soluble: water

Sparingly soluble: acetone, methanol Insoluble: Chloroform, n-hexane, diethyl ether (9) Color reaction:
Positive: Each reaction with potassium permanganate, iodine vapor and ceric sulfate 'Negative: Ehrlich's reaction, reaction with Dragendorff reagent and Molish's reaction

(10) Property of substance:
Amphoteric substance

(11) Color of crystals:
Yellow needles

(12) $^{13}$C-Nuclear magnetic resonance absorption spectrum: δ(ppm) (pyridine-d$^5$): 14.2, 17.3, 17.5, 19.4, 22.9, 31.1, 32.2, 33.5, 35.4, 36.1, 36.8, 40.2, 52.1, 55.6, 58.4, 64.6, 64.8, 68.3, 68.5, 70.5, 70.8, 72.2, 76.6, 78.1, 98.5, 107.1, 108.5, 121.6, 124.6, 124.9, 127.6, 131.0, 131.9, 132.4, 133.7, 137.0, 138.8, 155.1, 156.4, 162.5, 166.4, 174.7, 179.8, 187.3.

(13) Thin layer chromatography (silica gel sheet)

| Solvent | Rf value |
| --- | --- |
| (a) A mixture of isopropylalcohol, water and 28% aqueous ammonia (70:30:1) | 0.5 |
| (b) A mixture of n-butanol, acetic acid and water (4:1:2) | 0.3 |

The FR-900447 has antitumor activity and antimicrobial activity. Accordingly, the FR-900447 and its pharmaceutically acceptable salt are useful as an antitumor agent or antimicrobial agent which is used for the treatment of infectious diseases or tumor in human beings and animals.

As an example for showing such pharmacological effects of the FR-900447, some pharmacological test data are illustrated in the followings.

Test 1 (Antitumor activity)

The antitumor activity of FR-900447 was determined in experimental tumor system in mice.

Melanotic melanoma B16 was implanted intraperitoneally into adult female C$_{57}$BL/6 mice at an inoculum size of 0.9×10$^6$ cells per mouse. Twenty-four hours after the implantation of tumor cells, graded doses of FR-900447 were administered to mice intraperitoneally. Treatments were given twice a day on 1, 2 and 3 day(s) after the tumor inoculation.

Control animals received intraperitoneal doses of only physiological saline solution.

The injection volume was 0.2 ml in all experiments. Five mice were used for each experimental group.

Antitumor activity was evaluated by the mean survival times of a group of mice and also expressed by the T/C % value (mean survival time of treated group/mean survival time of control group×100). Toxity was measured as weight loss between 0 and 4 day(s) after tumor inoculation. The result is shown in Table 1. FR-900447 was quite active against the melanotic melanoma B16. Doses between 6.0-200 mg/kg resulted in significant increase in life span in mice.

TABLE 1

| | Dose mg/kg/day | Weight change (g) Day 0–Day 4 | Mean survival time (days) | T/C % |
| --- | --- | --- | --- | --- |
| FR-900447 | 200 | −0.8 | 22.4 | 149 |
| | 100 | +1.0 | 25.2 | 168 |
| | 50 | +1.1 | 26.8 | 184 |

TABLE 1-continued

| | Dose mg/kg/day | Weight change (g) Day 0–Day 4 | Mean survival time (days) | T/C % |
| --- | --- | --- | --- | --- |
| | 25 | +0.4 | 25.2 | 168 |
| | 12.5 | +1.0 | 25.2 | 169 |
| | 6.0 | +1.7 | 19.8 | 132 |
| Control | | +1.5 | 15.0 | 100 |

C$_{57}$BL/6 mouse, female, 7 week
tumor site: i.p (0.9×10$^6$ cells/mouse)
drug route: i.p [treatment twice a day on 1,2 and 3 day(s)]
five mice per group Test 2 (Antimicrobial Activity)

Antimicrobial activity of FR-900447 was determined by a serial broth dilution method in bouillon media. Minimum inhibitory concentration (MICs) were expressed in terms of mg/ml after overnight incubation at 37° C.

The result is shown in Table 2.

| Microorganisms | MIC (mg/ml) |
| --- | --- |
| *Staphylococcus aureus* 209 P | 1 |
| *Bacillus subtilis* | 0.25 |

Acute toxicity (LD50) of FR-900447 in ddY mice by intraperitoneal injection was about 1 g/kg.

The FR-900447 of this invention in admixture with pharmaceutically acceptable carriers can be administered to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of glycyrrhizin, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the object compound is to be varied depending on various factors such as kind of diseases, weight and/or age of a patient, and further the kind of administration route.

The optimal dosage of FR-900447 is usually selected from a dose range of 1 mg–1 g/kg/day, preferably 10 mg–500 mg/kg/day.

The following Example is given for the purpose of illustrating this invention.

EXAMPLE

A seed medium (160 ml) containing 1% corn starch, 1% glycerin, 0.5% glucose, 1% cottonseed meal, 0.5% yeast extracts, 0.5% corn steep liquor and 0.2% $CaCO_3$ (pH 6.5) was poured into each of three 500 ml Erlenmeyer flasks and sterilized at 120° C. for 30 minutes. A loopful of slant culture of *Streptomyces rubropurpureus* No. 6362 was inoculated to each of the medium and cultured at 30° C. on a rotary shaker with 3-inch throw at 200 rpm for 3 days. The resultant culture was inoculated to the same seed medium (80 liters) in a 200 liter jarfermentor, which had been sterilized at 120° C. for 30 minutes, and cultured at 30° C. for 2 days under aeration of 80 liters/mins and agitation of 265 rpm. Thirty five liters of the seed culture was inoculated to the production medium (1700 liters) containing 2% sucrose, 1.5% peanut powder, 0.5% yeast extracts, 0.00005% NaI and 0.0004% $CoCl_2.6H_2O$ in a 2000 liters stainless steel fermentor, which had been sterilized at 120° C. for 30 minutes and cultured at 30° C. for 4 days under aeration of 1760 liters/min. and agitation of 180 rpm.

The cultured broth thus obtained was filtered with an aid of diatomaseous earth (5 kg). The filtrate obtained (1750 l) was adjusted to pH 7.0 with 6N-NaOH and passed through a macroporous nonionic adsorption resin, Diaion HP-20 (trademark, made by Mitsubishi Chemical Industries) column (75 l). The column was washed with water (150 l) and then with 25% acetone (150 l), and eluted with 50% acetone (150 l). The active fraction was concentrated in vacuo to a volume of 20 liters and adjusted to pH 10 with 25% aqueous ammonia. The solution was added 40 liters of n-butanol and stirred for 10 minutes. This extraction procedure was repeated twice and the extracts were combined. Then the extracts were concentrated in vacuo to a volume of 500 ml. The oily materials obtained were mixed with silica gel (2 liters) and applied to a column chromatography using silica gel (5 liters). The column was eluted with 18 liters of methanol. The active fractions were concentrated in vacuo to dryness.

The crude sample was dissolved in 100 ml of 60% methanol containing 10 mM ammonium acetate and subjected to chromatography of a $C_{18}$-coated silica gel, NS gel (trademark, made by Nihon Seimitsu Kagaku Co., Ltd.) column (750 ml) developed with 5 liters of 60% methanol containing 10mM ammonium acetate. The active fractions eluted were concentrated in vacuo to a volume of 1 liter and passed through a column of Diaion HP-20 (300 ml). After washing with water, the column was eluted with 50% acetone (1 liter). The active fraction was evaporated to dryness under reduced pressure to give purified active materials as free base (5.7 g). Yellow crystals of FR-900447 substance (4 g) were obtained from hot methanol.

We claim:

1. A compound, FR-900447, or pharmaceutically acceptable salt thereof having the following characteristics as its free form:
   (1) has an elementary analysis (%): C59.05; H6.72; N5.57
   (2) has a molecular weight: 928 [SIMS: m/z 929 $(M^+ + 1)$]
   (3) has a melting point: 85° C. (dec.)
   (4) has an optical rotation: $[\alpha]_D^{23°} = +291.4°$ (C=0.675, $H_2O$)
   (5) has a characteristic ultraviolet absorption spectrum:
   $\lambda_{max}^{H2O} = 276$ nm ($E_{1cm}^{1\%}390$) 340 nm (sh) ($E_{1cm}^{1\%} = 80$)
   $\lambda_{max}^{H2O+HCl} = 272$ nm ($E_{1cm}^{1\%} = 400$), 330 nm (sh) ($E_{1cm}^{1\%} = 82$)
   $\lambda_{max}^{H2O+NaOH} = 243$ nm ($E_{1cm}^{1\%}275$), 278 nm ($E_{1cm}^{1\%} = 350$), 410 nm ($E_{1cm}^{1\%} = 31$)
   (6) has a characteristic infrared absorption spectrum:
   $\nu_{max}^{KBr} = 3400$, 2950, 1650, 1560, 1465, 1435, 1395 (sh), 1375, 1280, 1150, 1075, 1040 (sh), 960, 895, 855, 840 $cm^{-1}$
   (7) has a characteristic nuclear magnetic resonance absorption spectrum:
   δppm (pyridine-$d_5$): 10.62 (1H, t, J=6Hz), 8.38 (1H, s), 8.14 (1H, s), 6.90 (1H, s), 6.895 (1H, d, J=5 Hz), 6.43 (1H, s), 5.79 (1H, m), 5.80 (1H, d, J=10 Hz), 5.37 (1H, d, J=5 Hz), 4.48 (1H, q., J=6 Hz), 4.15 (1H, m), 3.9 (2H, m), 3.85 (1H, s), 3.63 (1H, t, J=10Hz), 3.47 (1H, m), 3.34 (1H, m), 3.12 (1H, m), 3.08 (2H, m), 3.07 (3H, s), 2.9 (1H, m), 2.82 (2H, m), 2.76 (6H, s), 2.74 (1H, m), 2.50 (6H, s), 2.19 (3H, s), 1.71 (3H, d, J=6Hz), 1.63 (2H, m), 1.62 (3H, d, J=6Hz), 1.47 (3H, d, J=5.4 Hz), 1.20 (3H, s)
   (8) is soluble in water, and is sparingly soluble in acetone and methanol, and is insoluble in chloroform, n-hexane and diethyl ether
   (9) is positive in color reaction with each of potassium permanganate, iodine vapor and ceric sulfate and is negative in Ehrlich's reaction, reaction with Dragendorff reagent and Molish's reaction
   (10) has a characteristic $^{13}C$-nuclear magnetic resonance absorption spectrum:
   δ(ppm) (pyridine-$d^5$): 14.2, 17.3, 17.5, 19.4, 22.9, 31.1, 32.2, 33.5, 35.4, 36.1, 36.8, 40.2, 52.1, 55.6, 58.4, 64.6, 64.8, 68.3, 68.5, 70.5, 70.8, 72.2, 76.6, 78.1, 98.5, 107.1, 108.5, 121.6, 124.6, 124.9, 127.6, 131.0, 131.9, 132.4, 133.7, 137.0, 138.8, 155.1, 156.4, 162.5, 166.4, 174.7, 179.8, 187.3.

2. A process for the production of FR-900447 as defined in claim 1, which comprises culturing the microorganism *Streptomyces rubropurpureus* FERM BP-584 in an aqueous nutrient medium under aerobic condition until substantial antimicrobial activity is imparted to said medium, and recovering FR-900447 from the resultant cultured broth.

3. An antimicrobial pharmaceutical composition which comprises an antimicrobially effective amount of a compound, FR-900447 as defined in claim 1, or pharmaceutically acceptable salt thereof and a non-toxic, pharmaceutically acceptable carrier.

* * * * *